(12) United States Patent
Kumar

(10) Patent No.: US 6,518,328 B2
(45) Date of Patent: Feb. 11, 2003

(54) COATED RESORBABLE POLYMER AND METHOD OF MAKING THE SAME

(75) Inventor: Mukesh Kumar, Warsaw, IN (US)

(73) Assignee: Biomet, Inc., Warsaw, IN (US)

( * ) Notice: Subject to any disclaimer, the term of this patent is extended or adjusted under 35 U.S.C. 154(b) by 0 days.

(21) Appl. No.: 09/738,615

(22) Filed: Dec. 15, 2000

(65) Prior Publication Data

US 2002/0127391 A1 Sep. 12, 2002

(51) Int. Cl.[7] .................................................. A61F 2/00
(52) U.S. Cl. ........................ 523/113; 428/325; 523/115; 524/417
(58) Field of Search ................................. 523/113, 115; 524/417; 428/325

(56) References Cited

U.S. PATENT DOCUMENTS

| | | |
|---|---|---|
| 4,512,038 A | 4/1985 | Alexander et al. |
| 5,006,120 A | 4/1991 | Carter |
| 5,197,966 A | 3/1993 | Sommerkamp |
| 5,211,664 A * | 5/1993 | Tepic et al. .................... 623/16 |
| 5,290,281 A | 3/1994 | Tschakaloff |
| 5,586,985 A | 12/1996 | Putnam et al. |
| 5,607,427 A | 3/1997 | Tschakaloff |
| 5,718,704 A | 2/1998 | Medoff |
| 5,779,706 A | 7/1998 | Tschakaloff |
| 5,968,047 A | 10/1999 | Reed |

* cited by examiner

Primary Examiner—Edward J. Cain
(74) Attorney, Agent, or Firm—Harness, Dickey & Pierce, P.L.C.

(57) ABSTRACT

A bioresorbable material is disclosed having a ceramic and polymer coating. The ceramic and polymer coating increases the tailorability of resorption rates and properties and increases design flexibility by virtue of its simplicity.

20 Claims, 3 Drawing Sheets

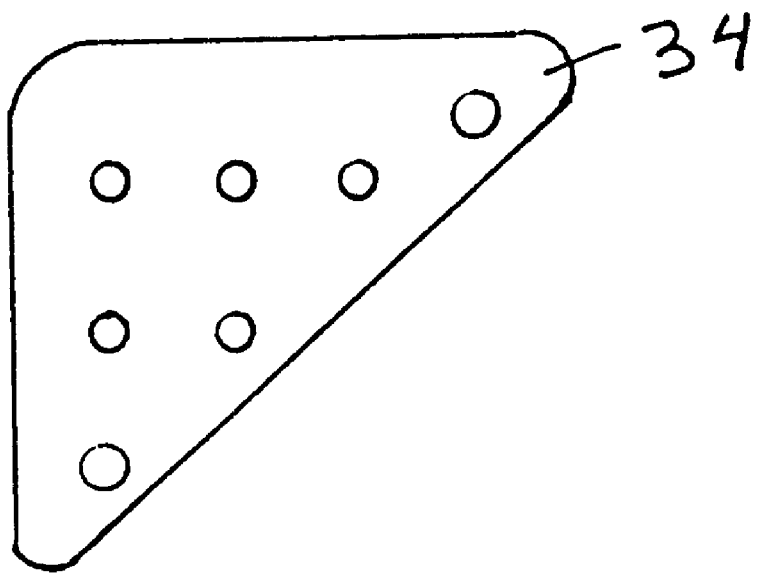

COATED RESORBABLE POLYMER AND METHOD OF MAKING THE SAME

BACKGROUND OF THE INVENTION

1. Technical Field

This invention generally relates to coated polymer materials and, more particularly, to a resorptive polymer coat having a ceramic polymer blend which, when used individually or in combination, provides a highly tunable resorption time and a means of supplying bone forming elements.

2. Discussion

The repair of separated or dislocated bone fragments or segments following bone surgeries requires realignment of the separated or dislocated fragments or segments and subsequent secure fixation for promoting proper natural rejoinder of these bone fragments or segments. The presence of relative motion of the bone fragments or segments at a fracture or osteotomy location may result in irritation of the surrounding tissues, nonunion between the bone fragments, and an extension of the time of fracture healing. It is therefore desirable to accomplish as completely as possible an immobilization of the fracture or osteotomy site. This involves the relative fixation of affected bone segments relative to each other and in relation to the surrounding bone structure.

Known methods for providing fixation between adjacent bone portions have included the use of metallic plates of varying configurations, which are secured across osteotomies or fracture sites by metallic bone screws. These devices have been made of biocompatible metals and metal alloys, such as commercially pure titanium, stainless steel and cobalt chrome molybdenum. Other materials and devices, such as wires, intramedullary nails or externally fixed pins have also been used to reduce bone fracture mobility and to improve the relative position of adjacent segments. The aim of fixation of adjacent bone portions is to immobilize the fracture or osteotomy sites in order to promote localized bone growth in the natural repair of the separation.

The disadvantages associated with the use of metallic and metallic alloy devices relate to the possible undesirable cosmetic results associated with the protrusion of these devices above the bone surface, especially in locations directly beneath the skin, that is, without any intervening soft tissue for masking the implant devices from being noticed externally. As such, the only way to remove these implant devices involves revision surgery after the localized bone area has healed. In addition, metal and metallic alloy devices often should be removed from a pediatric patient so as to prevent growth restrictions. Another disadvantage associated with using metallic implants is the lack of load transfer. As the fracture site heals, load bearing capability should transfer from the implant to the surrounding tissue. This is possible only with resorbable materials.

The use of medical implant devices made from bioresorbable materials has been described in literature and these devices have the advantage of being absorbed by the body over a period of time so as to allow for bone or fibrous material to become repaired at a fracture or osteotomy site by growing into the space created between adjacent bone portions. Many bioresorbable materials have been suggested for use in fixation of adjacent bone portions. It was believed that these materials had to be extremely strong to fixate the bone portions over a relatively long period of time. This typically meant that the osteosynthesis plate had to be relatively thick and be made out of a high molecular weight oriented material such as poly L-lactic acid in which the molecular weight would exceed 250,000. See Pihlajamaki, H., et al., "Absorbable Pins of Self-Reinforced Poly-L-Lactic Acid for Fixation of Fractures and Osteotomies," Journal of Bone and Joint Surgery, v. 74-B, n. 6, p. 853–857, November 1992. In addition, it was believed that certain copolymers of glyceride and lactide were not appropriate for use in osteosynthesis plates because of a rapid loss of mechanical strength. Grijpma, D. W., et al., "Poly (L-lactide) Crosslinked with Spiro-bis-dimethylenecarbonate," Polymer, v. 34, n. 7, 1993 at 1496.

While others suggest the use of non-reinforced materials, the molecular weight of the material had to be increased to maintain strength. In this regard, one author suggested using a non-oriented material having an average molecular weight of $10^6$. See Bos, R .R .M., et al., "Late Complications related to Bioresorbable Poly (L-Lactide) Plate-Osteosyntheses", Journal of Oral Maxillofacial Surgery, Supp. 3, 51(a) 1993 at 190. However, there were certain problems which were associated with these particular osteosynthesis plates. First, such osteosynthesis plates tended to have a relatively high degree of inflammatory response and therefore had to be removed from the patient. See, Bostman, O., "Current Concepts Review—Absorbable Implants for the Fixation of Fractures," Journal of Bone and Joint Surgery, pp. 148–153, 1991. In addition, the osteosynthesis plates had to be made relatively thick so as to provide the requisite strength and resorption time, which tended to make the osteosynthesis plates have an unwanted cosmetic appearance when implanted.

A need therefore exists for a bioresorbable fastening device for bone fixation, such as an osteosynthesis plate, that is thin enough and of a suitable material to be resorbed over a desired period of time, yet is of sufficient strength to maintain relative bone fixation over the time period needed for the natural repair of fractures or osteotomies between adjacent bone portions. A need also exists for a bioresorbable osteosynthesis plate which has adaptable resorption rates, composition, and strength. A need further exists for such a bioresorbable device to allow for the formation of one or more additional fastener openings at one or more required precise locations during the surgical procedure.

SUMMARY OF THE INVENTION

In accordance with the teachings of the present invention, a bioresorbable material is disclosed having a ceramic and polymer coating. The ceramic and polymer coating increases the tailorability and tuneability of resorption rates and properties and allows for increases in implant design flexibility by virtue of its simplicity. Also as the coating comprises of a resorbable ceramic, it helps in bone integration and formation.

In one preferred embodiment, a resorptive material includes a polymer and ceramic coating to control the osseoconductive properties of the coating. A resorbable ceramic powder is deposited onto a substrate by use of a resorbable polymer binder. It is possible to use a combination of differing ceramic compositions as well as ceramic powder particle sizes to adjust resorption properties. Similarly, it is possible to use a combination of resorbable polymeric binders in different amounts to adjust resorption time.

In another preferred embodiment, a material having a biocompatible resorbable ceramic with biologically acceptable cations such as calcium, sodium, potassium and anions of phosphates in various oxidation states, carbonates, bicarbonates and sulfates including but not limited to calcium sodium phosphate, calcium sulfate, hydroxyapatite, calcium carbonate, tricalcium phosphate and octacalcium phosphate or a mixture of resorbable ceramics.

In yet another preferred embodiment, a method of forming a resorbable coating material onto a substrate is disclosed. The method includes the steps of forming a mixture of the polymer binder, a resorbable ceramic powder and a solvent. The mixture is disposed onto the substrate at a fixed thickness. The solvent is either extracted or evaporated off, leaving a coating of ceramic powder coupled to the substrate by a polymer binder.

Use of the present invention provides a substrate material coated with a resorbable layer that affects resorption rate. The coating material is formed of a resorbable polymer binder and resorbable ceramic materials. By adjusting the volume fraction of the ceramic, the thickness of the coating, the molecular weight of the binder and the composition of the binder, the resorption rate of the coating can be significantly slowed down. As a result, the aforementioned disadvantages associated with the currently available resorbable materials have been substantially reduced or eliminated.

BRIEF DESCRIPTION OF THE DRAWINGS

The various advantages of the present invention will become apparent to one skilled in the art upon reading the following specification and by reference to the drawings in which:

FIG. 4 is a bone plate formed of the coated material of the invention.

DETAILED DESCRIPTION OF THE PREFERRED EMBODIMENTS

The following description of the preferred embodiments are merely exemplary in nature and are in no way intended to limit the invention, or its application, or uses. Moreover, while various specific substrate and coating structures are disclosed, it will be understood by those skilled in the art that they are merely exemplary and other specific substrate structures and coating may be used.

Figure 1:
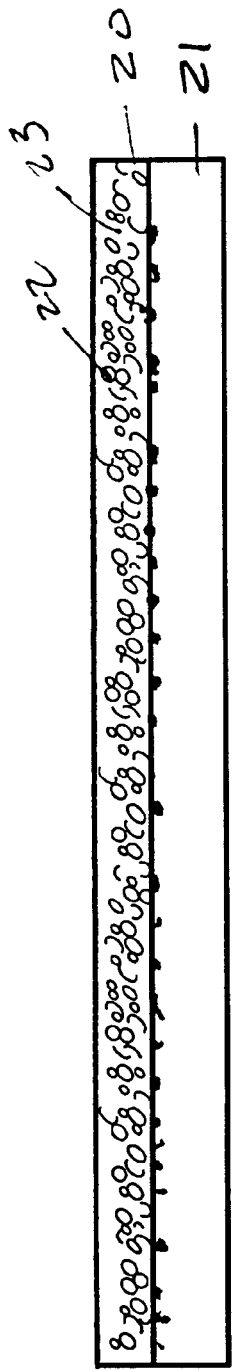
FIG. 1 is a cross-section of a coated substrate conforming to the teachings of the current invention.

FIG. 1 discloses a coating 20 of the current invention disposed on a substrate 21. The primary constituent of the coating 20 is ceramic powder 22. Generally, the ceramic powder 22 is a bio-compatible resorbable ceramic with cations of calcium, sodium potassium and anions of phosphates in various oxidation states. Preferably, the ceramic 22 is a phosphate, carbonate, bicarbonate or sulfate including but not limited to calcium sodium phosphate, calcium sulfate, hydroxyapatite, calcium carbonate, tricalcium phosphate and octacalcium phosphate or mixtures of these resorbable ceramics.

The particle sizes of the embedded ceramic 22 being used for the coatings 20 are generally below 200 microns. It is preferable that the particles have a mean size of 50 microns with a distribution of about 25 microns. It is possible to use tailored size distribution such as a bimodal particle size distribution to modify the overall performance of the device.

The coating 20 disclosed does not require the use of a ceramic powder binder 23 in the usual sense. In normal ceramic processing, binders (usually some kind of polymer) are used to hold the ceramic powder together but later burnt off during the firing and sintering stages. The subsequent sintering processes ensure structural integrity of powder formed ceramics by joining the individual powder particles together.

The binders 23 used in the present invention, and for that matter substrate polymers, are biocompatible and resorbable polymers, copolymers or blends such as those composed of lactic acid, glycolic acid, amides, anhydrides, orthroesters, dioxanones and many others. The weight percentage and molecular weight of the binder 23 is chosen to affect the resorption rate of the final structure. As opposed to normal binders used in the formation of ceramic structures, the binders 23 are not removed from the resulting structure by means of heat and oxidation. The binder materials 23 remain within the structure until resorbed after implantation.

The binder material 23 is combined with the ceramic powder 22 by the use of a solvent 24. The binder polymer 23 is dissolved within the solvent 24 and the ceramic powder 22 is added to form a slurry. The composition of the slurry preferably holds the ceramic powder 22 in suspension in the dissolved polymer/solvent mixture. There may be no chemical interaction between the ceramic powder 22 and this solution. In general, this slurry can also have pore forming agents such as sugar (sucrose or dextrose), salt (sodium chloride or carbonate and bicarbonate) and biologically active agents. The slurry may also have bio-compatible deflocculating agents (usually less than a 1% if any) to assist in keeping the ceramic particles held in suspension in the solvent 24.

Some of the usual solvents 24 that can be used are but not limited to acetone, pyrrolidone such as N-methyl-2-pyrrolidone, ethyl acetate and ethyl lactate. It is possible to use a mixture of solvents to adjust the density and viscosity of the solution as well as the amount of polymer binder to be dissolved. As with all biomedical applications, the solvents used should be benign and least toxic. As such, the solvent must be removed by well known processes such as vacuum drying or super critical extraction.

Usually the binder polymer 23 in the slurry is the same as the substrate polymer 21 which is to be coated. It is also envisioned that the binder polymer 23 can be different than the substrate polymer 21. Medical application demands that the binder 23 and substrate polymer 21 be bio-compatible and resorbable. In the event that the binder and substrate polymers are different, the solvent (or mixture of solvents) to be used must be able to dissolve or at least make both the substrate polymer 21 and the binder material 23 sticky.

If the solvent were removed by evaporation, extraction or leached into another medium before application to the substrate 21, a composite structure would form of resorbable ceramic powder 22 in a resorbable binder polymer matrix 23. This ceramic powder 22 is bound in the polymer matrix 23 of the precipitated resorbable polymer, leaving a resorbable composite which can be used as an implant.

When the slurry is poured onto the substrate polymer 21 and is allowed to evaporate on the substrate polymer 21, the solvents in the slurry also partially dissolves the substrate polymer 21. Eventually, the solvent will evaporate leaving the ceramic powder 22 bound by the binder 23 and partially dissolved substrate polymer 21.

The ratio of the binder polymer 23 to the solvent 24 can have a wide range, from very dilute to saturation. If LACTOSORB, offered by Biomet, Inc. of Warsaw, Ind., is used as binder polymer 23, the ratio of the binder polymer 23 to solvent 24 is between 9 to 12 g to 100 ml acetone. For saturation, the ratio is 15 g/100ml acetone. In this range of solution composition, the other variable is the ceramic powder 22 volume fraction. By varying the weight percentage of ceramic powder 22 to binder polymer 23, the percentage of polymer matrix 23 in the resulting product can be adjusted. So, the slurry could have a composition of dilute to saturated solution with particle volume fraction ranging from sparse to heavy.

The preferred composition of the slurry will depend on the application or the characteristics of the coating. Intuitively, if a longer resorption time were required, the binder polymer 23 would be close to saturation (almost 15 g of LACTOSORB per 100 ml acetone. For devices showing faster resorption, a lower concentration solution would be used. The other variable i.e., ceramic powder 22 volume fraction should not affect resorption rate, but the ceramic composition will affect resorption characteristics.

Figure 2:
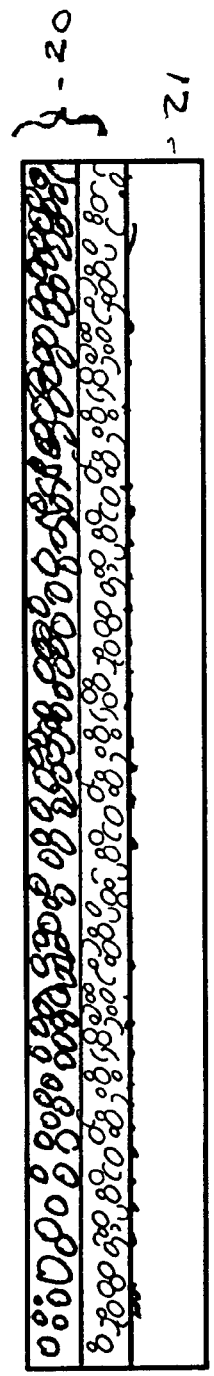
FIG. 2 is a cross-section of a multi-layer coating conforming to the teachings of the current invention.

As can be seen in FIG. 2, several coating layers can be applied to the substrate. These layers can be in any order and can have varying ceramic volume fractions ranging from none to heavy loading as well as varying powder size. By varying the ceramic material, and the binder, resorption rates can be varied.

Figure 3:
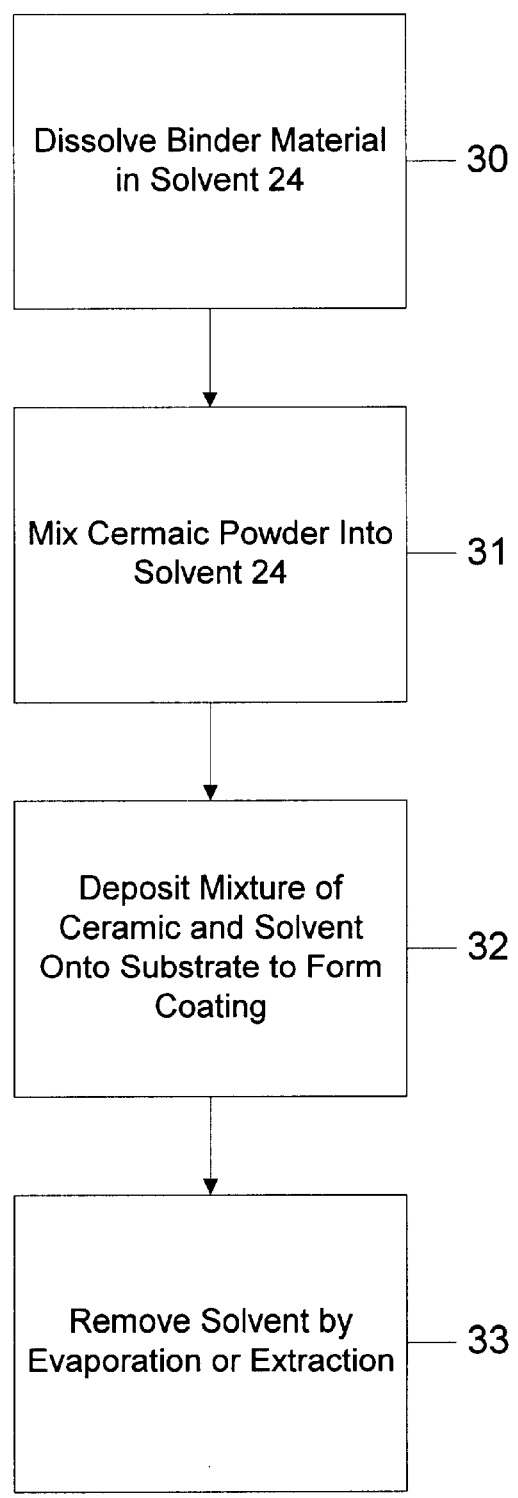
FIG. 3 is a flow chart describing the method of producing the coating of the invention.

As seen in FIG. 3, the biocompatible resorbable ceramic coating 20 is formed as follows. In process step 30, a binder polymer 23 is dissolved within a solvent 24. In process step 31, the ceramic powder 22 is mixed into the solvent 24 material so as to hold the ceramic powder 22 in suspension. Deflocculating additives may be used to hold the ceramic powders 22 in suspension within the mixture. In process step 32, the mixture is then deposited onto a substrate material 21. Should the substrate material 21 be of a polymer which is dissolvable by the particular solvent used, the surface layer of the substrate material begins to dissolve. In process step 33, the solvent is removed by evaporation. The ceramic particles 22 are then imbedded within the dissolved surface layer of the substrate as well as in the binder material. As the ceramic powder 22 is bound into the surface of the substrate 21, a mechanical lock is formed. If so desired, the slurry may be cast on a glass or other substrate with or without the benefit of spreading assisted by spinning. In such a case, instead of a coating, laminated structures of resorbable ceramic-polymer composites are fabricated. As before, the individual laminates can have varying particle size distribution, loading and composition.

Pore forming agents can be added to the solvent. These agents function to create pores within the binder material and allow for a variation of the resorption time.

Accordingly, a resorbable substrate material 21 having a resorbable polymer ceramic coating 20 is formed. The coating allows a user to adjust the resorption rate of the material. As seen in FIG. 4, a standard bone plate 34 is shown using the aforementioned material. Specifically, the resorption rate of a bone plate used in orthopedic procedures of the current invention can have tailorable resorption properties. The variable resorption rates lead to a significant benefit not seen in prior bone plate structures. For example, the resorption of the bone plate can be significantly slower than those bone plates formed by the substrate material alone. In particular, this can be useful in patients where bone regrowth would be expected to be much slower and, therefore, the support caused by the bone plate would need to be utilized by the patient for a much longer period of time. As mentioned before, a judicious choice of resorbable ceramic would help by supplying bone building elements.

A wide variety of features can be utilized in the various material disclosed and described above. The foregoing discussion discloses and describes a preferred embodiment of the present invention. One skilled in the art will readily recognize from such discussion, and from the accompanying drawings that various changes, modifications, and variations can be made therein without departing from the true spirit and fair scope of the invention.

What is claimed is:

1. A coating for a substrate comprising:
   a granular resorbable ceramic; and
   a polymer binder coating, said coating being disposed on the substrate, wherein the ceramic and polymer binder coating is calcium sodium phosphate particles suspended in a polymer matrix.

2. A coating for a substrate comprising:
   a granular resorbable ceramic; and
   a polymer binder coating, said coating being disposed on the substrate, wherein the ceramic and polymer binder coating is ceramic particles suspended in a polymer matrix, and wherein the ceramic has cations of calcium and anions of phosphates in various oxidation states.

3. A coating for a substrate comprising:
   a granular resorbable ceramic; and
   a polymer binder coating, said coating being disposed on the substrate, wherein the ceramic and polymer binder coating is ceramic particles suspended in a polymer matrix, and wherein the ceramic has cations of sodium potassium and anions of phosphates in various oxidation states.

4. A coating for a substrate comprising:
   a granular resorbable ceramic; and
   a polymer binder coating, said coating being disposed on the substrate, wherein the ceramic and polymer binder coating is ceramic particles suspended in a polymer matrix, and wherein the ceramic is a material selected from the group of carbonate, bicarbonate, sulfate and mixtures thereof.

5. The coating for a substrate of claim 2 wherein the ceramic particles have a diameter of less than 200 microns.

6. A coating for a substrate comprising:
   a granular resorbable ceramic; and
   a polymer binder coating, said coating being disposed on the substrate, wherein the ceramic and polymer binder coating is ceramic particles suspended in a polymer matrix, and wherein the ceramic particles have a mean particle size of about 50 microns with an even distribution about 25 microns.

7. A coating for a substrate comprising:
   a granular resorbable ceramic; and
   a polymer binder coating, said coating being disposed on the substrate, wherein the ceramic and polymer binder coating is ceramic particles suspended in a polymer matrix, and wherein the ceramic particles have a tailored particle size distribution.

8. A resorbable material comprising:
   a substrate;
   a coating comprising a resorbable ceramic disposed in a polymer matrix, said coating disposed on said substrate wherein the ceramic is calcium sodium phosphate.

9. A resorbable material comprising:
   a substrate;
   a coating comprising a resorbable ceramic disposed in a polymer matrix, said coating disposed on said substrate wherein the ceramic has cations of sodium potassium and anions of phosphates in various oxidation states.

10. A resorbable material comprising:

a substrate;

a coating comprising a resorbable ceramic disposed in a polymer matrix, said coating disposed on said substrate wherein the ceramic is a material selected from the group carbonate, bicarbonate, sulfate and mixtures thereof.

11. A resorbable material comprising:

a substrate;

a coating comprising a resorbable ceramic disposed in a polymer matrix, said coating disposed on said substrate wherein the ceramic is ceramic particles having a diameter of less than 200 microns.

12. The resorbable material of claim 11 wherein the ceramic is ceramic particles having a mean particle size of about 50 microns with almost even distribution about 25 microns.

13. The resorbable material of claim 11 wherein the ceramic particles have tailored particle size distribution.

14. A method of forming a resorbable material for coating a substrate;

providing a ceramic powder;

providing a polymer binder;

providing a solvent;

mixing the polymer with the ceramic and solvent;

placing mixture onto the substrate; and removing the solvent, wherein providing a ceramic powder further includes providing a ceramic particle have a diameter of less than 200 microns.

15. The method of forming a resorbable material of claim 14 wherein providing a ceramic powder further includes providing ceramic particles have a mean particle size of about 50 microns with an even distribution about 25 microns.

16. The method of forming a resorbable material of claim 14 wherein providing a solvent further includes providing a solvent selected from the group of acetone, pyrrolidones, N-methyl-2-pyrrolidone, ethyl acetate and ethyl lactate.

17. The method of forming a resorbable material of claim 14 wherein providing a solvent further includes providing a deflocculating agent.

18. The method of forming a resorbable material of claim 14 wherein providing a solvent further includes providing a pore forming agent.

19. The method of forming a resorbable material of claim 14 further including the step of subjecting the material to centrifugal forces wherein the thickness of the mixture is reduced.

20. The method of forming a resorbable material of claim 19 further includes:

providing a second solvent;

mixing the polymer with the ceramic and second solvent;

placing a second layer of mixture onto the material;

subjecting the material to second centrifugal forces, wherein subjecting the material to second centrifugal forces controls the thickness of the second layer and thereby the resorption properties of the material.

* * * * *

UNITED STATES PATENT AND TRADEMARK OFFICE
CERTIFICATE OF CORRECTION

PATENT NO.     : 6,518,328 B2
DATED          : February 11, 2003
INVENTOR(S)    : Mukesh Kumar It is certified that error appears in the above-identified patent and that said Letters Patent is hereby corrected as shown below:

<u>Column 8,</u>
Line 3, "have" should be -- having --.

Signed and Sealed this

Seventeenth Day of June, 2003

JAMES E. ROGAN
*Director of the United States Patent and Trademark Office*